(12) United States Patent
Dahl et al.

(10) Patent No.: US 11,386,879 B2
(45) Date of Patent: Jul. 12, 2022

(54) AUDIO DEVICE WITH ADAPTIVE AUTO-GAIN

(71) Applicant: Invisio Communications A/S, Hvidovre (DK)

(72) Inventors: Jonas Burup Dahl, Ballerup (DK); Jan Larsen, Smørum (DK)

(73) Assignee: INVISIO A/S, Hvidovre (DK)

( * ) Notice: Subject to any disclaimer, the term of this patent is extended or adjusted under 35 U.S.C. 154(b) by 0 days.

(21) Appl. No.: 16/631,946

(22) PCT Filed: Jun. 20, 2018

(86) PCT No.: PCT/EP2018/066412
§ 371 (c)(1),
(2) Date: Jan. 17, 2020

(87) PCT Pub. No.: WO2019/015910
PCT Pub. Date: Jan. 24, 2019

(65) Prior Publication Data
US 2020/0184944 A1  Jun. 11, 2020

(30) Foreign Application Priority Data
Jul. 18, 2017  (DK) .......................... PA 2017 70579

(51) Int. Cl.
*G10K 11/178* (2006.01)

(52) U.S. Cl.
CPC .. *G10K 11/17827* (2018.01); *G10K 11/17823* (2018.01); *G10K 11/17873* (2018.01); *G10K 2210/1081* (2013.01); *G10K 2210/3056* (2013.01); *G10K 2210/3224* (2013.01)

(58) Field of Classification Search
CPC ....... G10K 11/17827; G10K 11/17823; G10K 11/17873; G10K 2210/1081; G10K 2210/3056; G10K 2210/3224
USPC ... 381/71.6, 71.11, 71.1, 373, 94.1, 92, 73.1
See application file for complete search history.

(56) References Cited

U.S. PATENT DOCUMENTS

| | | | |
|---|---|---|---|
| 7,903,825 B1 | 3/2011 | Melanson | |
| 7,983,907 B2 | 7/2011 | Visser | |
| 2008/0267416 A1* | 10/2008 | Goldstein | ............ H04R 1/1091 381/56 |
| 2010/0119077 A1 | 5/2010 | Platz | |

(Continued)

OTHER PUBLICATIONS

International Search Report and Written Opinion for International Application No. PCT/EP2018/066412, dated Jan. 24, 2019 (10 pages).

(Continued)

*Primary Examiner* — Vivian C Chin
*Assistant Examiner* — Con P Tran
(74) *Attorney, Agent, or Firm* — Nixon Peabody LLP

(57) ABSTRACT

An audio device for receiving radio communication. The audio device is configured to receive radio communication as a received radio signal. The audio device includes a hear-through element configured to provide a hear-through signal to a user in response to a received ambient sound signal, and an adaptive auto-gain element configured to perform an auto-gain function of the received radio signal according to an adaptive gain value resulting in a modified radio signal, and to set the adaptive target level for the auto-gain function in response to the hear-through signal.

20 Claims, 3 Drawing Sheets

(56) References Cited

U.S. PATENT DOCUMENTS

2015/0016633 A1  1/2015  Gao
2016/0365082 A1  12/2016 Poulsen

OTHER PUBLICATIONS

International Preliminary Report on Patentability in International Application No. PCT/EP2018/066412, dated Oct. 21, 2019 (14 pages).

* cited by examiner

AUDIO DEVICE WITH ADAPTIVE AUTO-GAIN

CROSS-REFERENCE TO RELATED APPLICATIONS

This application is a U.S. National Stage of International Application No. PCT/EP2018/066412, filed Jun. 20, 2018, which claims the benefit of Denmark Patent Application No. PA 2017 70579, filed Jul. 18, 2017, both of which are incorporated herein by reference in their entireties.

FIELD OF THE INVENTION

The present invention relates generally to an audio device, such as a hearing protection device, headset, etc. for receiving radio communication, where the audio device comprises a hear-through element configured to provide a hear-through signal to a user in response to a received ambient sound signal.

BACKGROUND OF THE INVENTION

Many different types of hearing protection devices provide passive or active hearing protection in various ways for a user in order to protect the user's hearing as generally known.

Additionally, certain types of headsets provide active noise reduction (ANR) to reduce ambient sound received by the user (considering it unwanted noise). ANR is also sometimes referred to as active noise cancellation (ANC), active noise suppression (ANS), etc. Such headsets are sometimes referred to as noise cancellation headsets and may e.g. be of the in-ear type or over-the-ear type.

Thus, hearing protection devices, headsets (e.g. ANR headsets), and similar will reduce, diminish, dampen, occlude, and/or etc. the ambient sound (the sound outside the particular device or headset) to various degrees for the user.

Some hearing protection devices and headsets provides a hear-through functionality where at least a part of the ambient sound is forwarded to the user's ear canal at or below a certain maximum noise level (at least within certain limits) to enable situational awareness. If the ambient sound increases above the maximum noise level, the hearing protection device or headset dampens the noise that is allowed to pass through to the ear canal to protect the user's hearing. At a point when the noise becomes too loud, leakage noise will eventually be heard by the user above the maximum noise level as sound eventually will propagate through the hearing protection device. The level of ambient sound, for when leakage noise will be heard by the user, is heavily dependent on specific design, materials, etc. of a particular hearing protection device and will often vary from type to type of hearing protection device.

Hear-through may be passive, e.g. providing a sound channel, sound tube, acoustic connection, or similar more or less openly (it may e.g. be mechanically occluded at least partially to offer hearing protection) connecting an interior with an exterior of a hearing protection device where sound in the interior typically is provided in or to the ear-canal of the user. Alternatively, hear-through may be active, e.g. picking up ambient sound by a microphone or similar located on or in the exterior of the hearing protection device and providing the picked up sound signal, e.g. dampened to protect the hearing of the user, to a speaker or similar located in the interior so that emitted sound of the speaker is provided in or to the ear canal of the user.

Hear-through functionality is for some uses very important for the situational awareness of the user, e.g. to be able to hear verbal communication, detect dangers, or to determine whether a given sound originates from the front or back and left or right of the user. This is especially the case for professional users, such as armed forces, firefighters, emergency workers, police, security personal, etc.

Some types of headsets also include a radio communications unit or element for at least receiving (e.g. also transmitting) radio communication or are at least connectable to receive radio communication from such a radio communications unit or element.

However, in relation to hearing protection devices, headsets, and/or other audio devices that include radio communication and where the hearing protection device, the headset, etc. has hear-through capability, the hear-through sound may very well interfere with the radio communication signal and vice versa to the detriment of the sound quality of either or even both.

Furthermore, auto-gain, as generally known, is used in certain sound applications to automatically increase sounds with low sound level (loudness) and decrease sounds with (too) high sound level (loudness), respectively, in relation to a target sound level. Auto-gain is sometimes also referred to as automatic gain control (AGC). Implementations of auto-gain may involve a closed-loop feedback regulating circuit providing controlled signal amplitude as output in spite of variations of the amplitude of the input signal.

Patent specification U.S. Pat. No. 7,983,907 discloses a headset with separation of speech signals using at least two microphones for the speech separation, e.g. using blind source separation, where one microphone is located closer to the mouth of a user than the other(s). When a two channel voice activity detector (VAD) detects speech, it generates a control signal that in some embodiments is used to by an automatic gain control (AGC) function applied to the output of a speech signal being transmitted by a transmission subsystem.

Patent application US 2016/0365082 relates to headphones with multiplexed microphone signals enabling active noise cancellation that includes an audio plug with four connectors with one connector connected to ground, one to a left speaker, one to a right speaker, and the last connector dedicated to convey signals from two or more microphones that are multiplexed onto a single connector. An automatic gain control (AGC) is mentioned, but only in relation to be provided directly on a sensor by providing an output impedance of a bias generator that is high at low acoustic levels and lower at higher acoustic levels.

OBJECT AND SUMMARY OF THE INVENTION

It is an object to provide an audio device with hear-through and radio communications that provides increased sound quality of received radio communication.

Additionally, an objective is to provide an audio device with hear-through and radio communications that avoids or at least reduces one or more of the drawbacks mentioned above.

A first aspect of the invention is defined in claim 1.

According to the first aspect, one or more of these objects is/are achieved at least to an extent by an audio device for (at least) receiving radio communication where the audio device is configured to receive radio communication as a received radio signal. The radio signal may be received from a source that is internal or alternatively external to the audio device (or a combination e.g. in case of receiving a plurality of radio signals from several radio sources). The audio device comprises a hear-through element configured to provide a hear-through signal (directly or indirectly) to a user. The hear-through signal is provided in response to a received ambient sound signal. The provided hear-through signal may be a dampened or a selectively dampened (i.e. it may be dampened only under certain circumstance) version of the received ambient sound signal. The received ambient sound signal may e.g. be obtained by a microphone or similar, an acoustic coupling, etc. In some embodiments, one or more sound attenuating elements dampens the outside ambient sound (at least as long as there is no leakage noise) except for the part that is provided by the hear-through signal. The one or more sound attenuating elements may e.g. be internal or alternatively external to the audio device. The hear-through element may be passive and/or active. The audio device further comprises an adaptive auto-gain element configured to perform an auto-gain function of the received radio signal according to an adaptive gain value, resulting in a modified radio signal, and to set the adaptive gain value for the auto-gain function in response to the hear-through signal. It is to be understood that the modified radio signal theoretically could be unmodified (by the auto-gain function) when the received radio signal is exactly on target/the gain value is exactly one.

In this way, a particular gain value for the auto-gain function for the received radio signal is adaptively set in response to the hear-through signal. This will increase the sound quality (clarity/speech intelligibility) of the radio communication signal since it then is possible to adjust the target sound level of the received radio signal depending on the sound level of the hear-through signal. The auto-gain gain value for the received radio signal may accordingly be increased when the sound level of the hear-through signal is relatively high that otherwise would or could make the received radio signal less intelligible for the user or even obscure the received radio signal. Additionally, the auto-gain gain value for the received radio signal may accordingly be decreased when the sound level of the hear-through signal is relatively low, which may conserve power and maintain listening comfort for a user while still providing an adequate sound level for the radio signal. Additionally, a user may set the target level for the source or element supplying the radio signal generally at a lower setting since the system automatically will increased the volume of the received radio signal in cases of noise. A generally lower volume setting will protect the user's hearing compared to having a general higher setting. The auto-gain gain value may, under certain circumstances e.g. as disclosed herein, also be maintained at a current level if the current level is sufficient.

In a way, for the received radio signal in 'isolation' the hear-through signal may be treated as noise (even though it is desirable or even significant to receive). For professional users, such as armed forces, firefighters, emergency workers, police, security personal, etc. it may be crucial to be able to clearly hear a received radio communication even in situations of noisy environments with high ambient sound levels that even may vary quite a lot in a given period of time. It is noted that (at least in some embodiments), the hear-through signal is not removed, which is also an advantage especially for professional users, thereby still enabling situational awareness.

Accordingly, the auto-gain element will adaptively adjust the gain value (and thereby the level of the received radio signal) in response to the hear-through signal. For a given currently set gain value (determined by a particular hear-through signal), the level of the modified radio signal (i.e. the 'output') is adjusted according to the gain value (now set, until it adaptively is changed as disclosed herein), i.e. the signal level or amplitude of the received radio signal (i.e. the 'input') is adjusted with the gain value to provide the modified radio signal. When the gain value is changed as disclosed herein, the level of the modified radio signal is adjusted according to the new gain value until it changes again, etc. This signifies, that a relatively low volume radio signal and a relatively high volume signal is applied with the same gain value as the setting of the gain value (at least in some embodiments) is independent of the received radio signal. This reduces complexity.

In some embodiments, the audio device comprises one or more sound attenuating elements. Alternatively, the one or more sound attenuating elements are external to the audio device, e.g. comprised by or connected to a device that comprises the audio device. As another alternative with a plurality of sound attenuating elements, at least one is internal and at least one is external to the audio device. The one or more sound attenuating elements may provide hearing protection for the user.

In some embodiments, the one or more sound attenuating elements comprises one or more passive hearing protection elements configured to dampen the received ambient sound signal and/or the hear-through signal.

In some embodiments, in addition or alternatively, the one or more sound attenuating elements comprises one or more active hearing protection elements configured to selectively dampen the received ambient sound signal and/or the hear-through signal, the selectively dampening of the received ambient sound signal and/or the hear-through signal being carried out according to one or more predetermined criteria.

In some embodiments, in addition or alternatively, the one or more sound attenuating elements comprises an active noise reduction (ANR) system configured to reduce or suppress noise in the received ambient sound signal and/or the hear-through signal.

In some embodiments, the adaptive auto-gain element is further configured to set the adaptive gain value for the auto-gain function in response to an estimated amount of leakage noise (generally only present to a significant degree for relatively high sound levels) present in an ear-canal of the user (i.e. in addition to the hear-through signal).

Leakage noise is the ambient sound that propagates through the audio device when the one or more sound attenuating elements (and e.g. housing of the audio device) no longer can remove or diminish the outside sound fully or sufficiently. For professional uses as mentioned elsewhere, it is not uncommon that leakage noises will be present from time to time. When leakage noise is present, at least above a certain level, it can also make the received radio signal less intelligible or obscured for the user. However, by adapting the gain value to take the leakage noise into account it is possible to at least mitigate the influence of the leakage noise.

In some embodiments, audio device is configured to
measure or estimate a sound level of the received ambient sound signal and/or the hear-through signal, and
derive the estimated amount of leakage noise in response to the measured or estimated sound level(s).

The estimated amount of leakage noise may e.g. be derived using a predetermined profile or similar, being specific for (the type, class, etc. of) the audio device or the device that comprises the audio device, such as a headset, hearing protection device, etc. where the predetermined profile or similar a priori establishes a relationship between measured or estimated sound level(s) and the expected leakage noise for the particular device. This provides an expedient way of estimating the leakage noise without having to obtain it directly.

In some embodiments, the adaptive auto-gain element is further configured to set the adaptive gain value for the auto-gain function in response to the received ambient sound signal (i.e. in addition to the hear-through signal). The received ambient sound signal, at least in some embodiments, corresponds or is a good representation of the leakage noise if/when present. The received ambient sound signal may e.g. be obtained by a microphone or similar located on or in the exterior of the audio device or the device that comprises the audio device, such as a headset, hearing protection device, etc. Alternatively, the received ambient sound signal may e.g. be obtained by a microphone or similar located in the interior of the audio device or the device that comprises the audio device. As yet another alternative, the received ambient sound signal may e.g. be obtained by an acoustic port or the like.

In some embodiments, the adaptive auto-gain element is configured to
 adaptively increase and decrease, respectively, the gain value for the auto-gain function as a function of the hear-through signal when the hear-through signal is below a predetermined first level, i.e. the gain value is increased for an increasing level of the hear-through signal and decreased for a decreasing level of the hear-through signal. The gain value stays the same if the hear-through signal stays the same (e.g. within certain limits).

In this way, the gain value for the modified radio signal is increased for increasing levels of the hear-through signal, which avoids or at least reduces the risk that the hear-through signal will interfere (too much) with the radio signal, and correspondingly, the gain value is reduced for decreasing levels of the hear-through signal ensuring that the radio signal does not interfere (too much) with the hear-through signal or gets too high for a user without any need.

This may correspond to a situation where the ambient sound does not create any leakage noise (or at least not any significant amount of leakage noise) and where the hear-through signal does not need to be dampened for safety reasons as given by the predetermined first level.

In some embodiments, the adaptive auto-gain element is configured to adaptively increase and decrease, respectively, the gain value for the auto-gain function as a function of the hear-through signal when the hear-through signal is below a predetermined first level and above another predetermined level.

The respective adaptive increase and decrease of the gain value may e.g. be a linear, non-linear, or a combination thereof, function of the hear-through signal. In addition or alternatively, the respective adaptive increase and decrease of the gain value may be a function of the leakage signal or the received ambient sound signal.

In some embodiments, the adaptive auto-gain element is configured to
 (substantially) maintain the gain value for the auto-gain function at a current level when the hear-through signal would otherwise be above but kept about a predetermined level (e.g. the predetermined first level mentioned above) (i.e. the hear-through signal would be above the first predetermined level without being dampened for safety reasons but it is dampened to maximally be at that level for the safety reasons) and the received ambient sound signal is below a predetermined second level.

Furthermore (at least some embodiments), instead of maintaining the gain value as a single value, it can be maintained within certain relatively smaller boundaries and/or tolerances.

This may correspond to a situation where the ambient sound does not create any (or any significant) leakage noise and where the hear-through signal actively and/or passively is dampened by one or more sound attenuating elements to be at a sound level in the ear canal of the user being at most the predetermined first level for safety reasons. In such a situation, a current gain value is sufficient as the hear-through signal is not increased further for safety reasons and leakage noise is not present or not an issue.

In some embodiments, the adaptive auto-gain element is configured to
 adaptively increase and decrease, respectively, the gain value for the auto-gain function (e.g. at least up to a maximum level) as a function of
   the hear-through signal, and/or
   the received ambient sound signal,
 when the received ambient sound signal is above a predetermined level (e.g. the predetermined second level mentioned above).

This may correspond to a situation where the ambient sound do create (significant) leakage noise and where the ambient sound cannot be dampened to be fully below the predetermined first level in the ear canal (due to the ambient sound being too large whereby leakage noise will be present in the ear canal), In this way, the gain value may be increased to reduce the effect of the leakage noise.

The respective adaptive increase and decrease of the gain value may e.g. be a linear, non-linear, or a combination thereof, function of the hear-through signal. In addition or alternatively, the respective adaptive increase and decrease of the gain value may be a function of the leakage signal or the received ambient sound signal.

The number of predetermined levels—governing intervals of different adaptation of the adaptive auto-gain element—may vary depending on use and/or implementation.

In some embodiments, the predetermined second level is larger than the predetermined first level. In some further embodiments, the predetermined first level is about 85 dB and/or the predetermined second level is selected from the range of about 95 dB to about 115 dB, is selected from the range of about 100 dB to about 110 dB, or is about 105 dB. However, the specific numbers, and in particular the number for the predetermined second level, may vary from design to design of the audio device or the device comprising the audio device. The first level may e.g. be defined according to hear-through specifications.

In some embodiments, the audio device is configured to maintain the gain value of the auto-gain function at a level providing optimised signal to noise ratio (SNR) between the received radio signal and an overall sound signal present in an ear canal of the user, the overall sound signal comprising at least the modified radio signal and the hear-through signal.

In some embodiments, the audio device comprises or is connected to a microphone located in the ear canal of the user, and wherein the signal to noise ratio is determined by measuring a level of the received radio signal or the modified (or potentially modified) radio signal and by measuring e.g. a level of the overall sound signal in the ear canal of the user. The level of the overall sound signal may e.g. be measured by a microphone or similar located in (connection with) the ear canal of the user, e.g. in an interior of an ear cup for a hearing protection device or headset.

In some alternative embodiments, the signal to noise ratio is determined in response to an estimate of the noise in the ear canal (e.g. measured by a microphone or similar located in (connection with) the ear canal of the user, e.g. in an interior of an ear cup). In some further embodiments, the signal to noise ratio is further determined in response to a type of the noise, e.g. as characterised by its frequency composition, the overall character of the noise (static, intermittent, low-frequency, etc.).

In some embodiments, the audio device comprises a radio communications element being configured to receive radio communication and supply the received radio signal.

In some alternative embodiments, the audio device is configured to receive the received radio signal from an external (i.e. external to the audio device) radio communications element.

In some embodiments, the audio device is
an active and/or passive hearing protection communication headset, and/or
an active noise reduction headset.

In some embodiments, the gain value as a function of the hear-through signal (and/or of the received ambient sound signal) is set or fitted in dependence to one or more functional capabilities and/or intended use.

In some embodiments, the hear-through element (or another digital signal processor) is further configured to perform one or more digital signal processing functions selected from the group consisting of:
occlusion,
providing increased situational awareness,
compensating for hearing loss,
providing additional radio signals from additional radio sources,
whisper-mode,
comfort mode,
environment detection and adaption,
noise reduction,
noise gate,
spatial filtering or beamforming,
volume control,
tinnitus maskers, voice prompts, or other injected audio signals,
noise cancellation, and
linear filtering.

In some further embodiments, the adaptive auto-gain element is configured to set the adaptive gain value for the auto-gain function in response to the received radio signal (i.e. in addition to at least the hear-through signal). Accordingly, the auto-gain function of the received radio signal will result in a further modified radio signal.

In this way, it is possible to take into consideration also the received radio signal, and in particular a level of the received radio signal.

In some further embodiments, the adaptive gain value for the auto-gain function is set (also) in response to a target level of the received radio signal.

In this way, the level of the received radio signal may be adjusted according to a target level, which e.g. may signify that a relatively low volume radio signal is applied with a different (e.g. greater) gain value than a gain value of a relatively high volume signal (e.g. being smaller).

The adaptive auto-gain element may be configured to receive the received radio signal, a sound level thereof, and/or the target level.

In some further embodiments, the gain value is not set in response to the hear-through signal, i.e. only in response to the received radio signal (and e.g. further signals).

BRIEF DESCRIPTION OF THE DRAWINGS

These and other aspects will be apparent from and elucidated with reference to the illustrative embodiments as shown in the drawings, in which:

FIG. 2 schematically illustrates an audio device as disclosed herein being part of an exemplary over-the-ear cup for a hearing protection device, headset, or similar;

DESCRIPTION OF PREFERRED EMBODIMENTS

Figure 1:
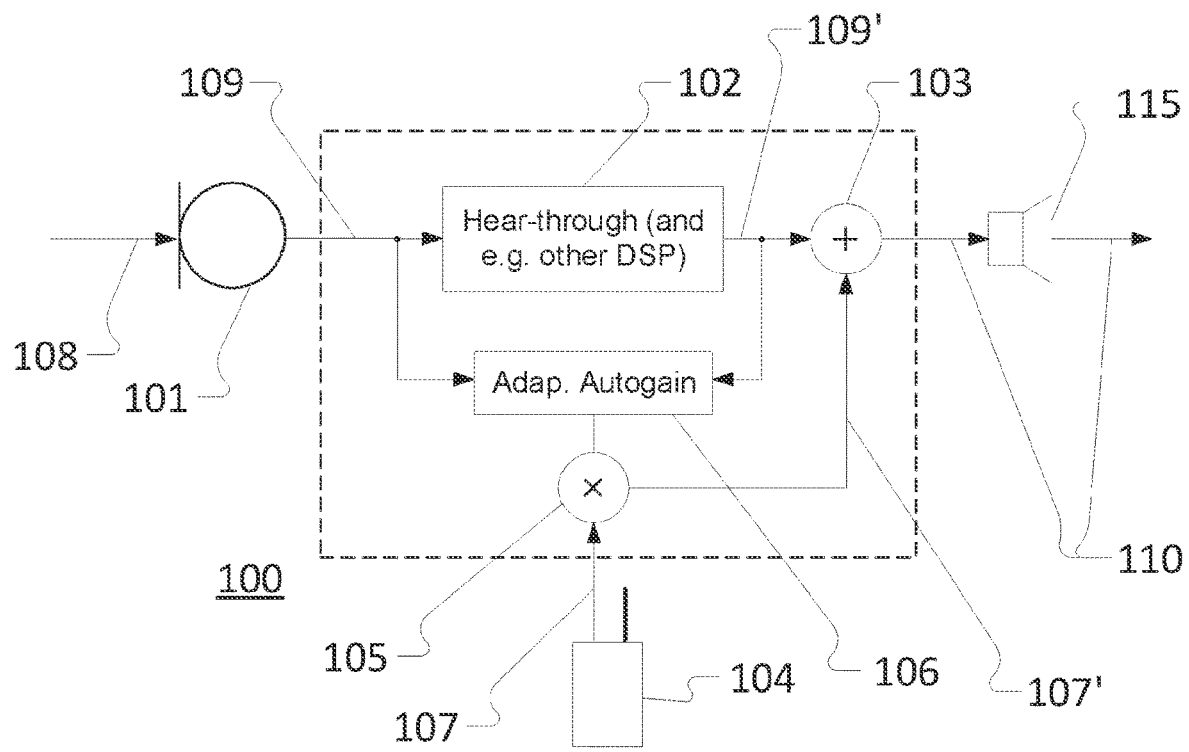
FIG. 1 schematically illustrates an audio device comprising an adaptive auto-gain element as disclosed herein according to one embodiment.

FIG. 1 schematically illustrates an audio device comprising an adaptive auto-gain element as disclosed herein according to one embodiment.

Schematically illustrated is an audio device 100 as disclosed herein comprising a hear-through element 102 as disclosed herein providing a hear-through signal 109' where the hear-through signal 109' is provided in response to a received ambient sound signal 108, 109. In the shown embodiment, a microphone 101 picks up the ambient sound 108 and provides it to the audio device 100 as the received ambient sound signal 109. The microphone 101 could alternatively be a part of the audio device 100. As a further alternative, the audio device 100 could have or be connected to an acoustic port or similar to obtain an ambient sound signal 109 acoustically from the ambient sound 108, i.e. without using a microphone.

In some embodiments, the hear-through signal 109' is a capped, by the hear-through element 102 and/or one or more sound attenuating elements, at a maximum level, also referred to as a predetermined first level (e.g. about 85 dB) to offer hearing protection for a user (see e.g. 303 in FIG. 3).

The audio device 100 further comprises an adaptive auto-gain element 106 as disclosed herein configured to perform an auto-gain function of a received radio signal 107. The received radio signal 107 is received from a radio communications element 104 being internal or as shown being external.

The adaptive auto-gain element 106 applies a gain factor to the received radio signal 107 by a multiplier circuit or element 105 according to a current gain value resulting in a modified (or potentially modified) radio signal 107' that is added together with the hear-through signal 109' using an adding element or circuit 103 resulting in overall sound signal 110 that is forwarded to a speaker or the like 115 producing sound in an ear canal of the user. The speaker 115 is shown as external to the sound device 100 but could alternatively be internal.

As disclosed herein, the adaptive auto-gain element 106 adjusts or controls the adaptive gain value of the received radio signal 107 in response to the hear-through signal 109' and the received ambient sound signal 109. In alternative embodiments, the adaptive auto-gain element 106 adjusts or controls the adaptive gain value of the received radio signal 107 in response to the hear-through signal 109' only.

The hear-through element 102 (and/or one or more other digital signal processors) may in some embodiments be further configured to perform one or more digital signal processing functions as disclosed herein.

The audio device 100 may be comprised by another device, such as a headset, hearing protection device, an ANR headset, etc. and e.g. as illustrated in connection with FIG. 2.

Figure 2:
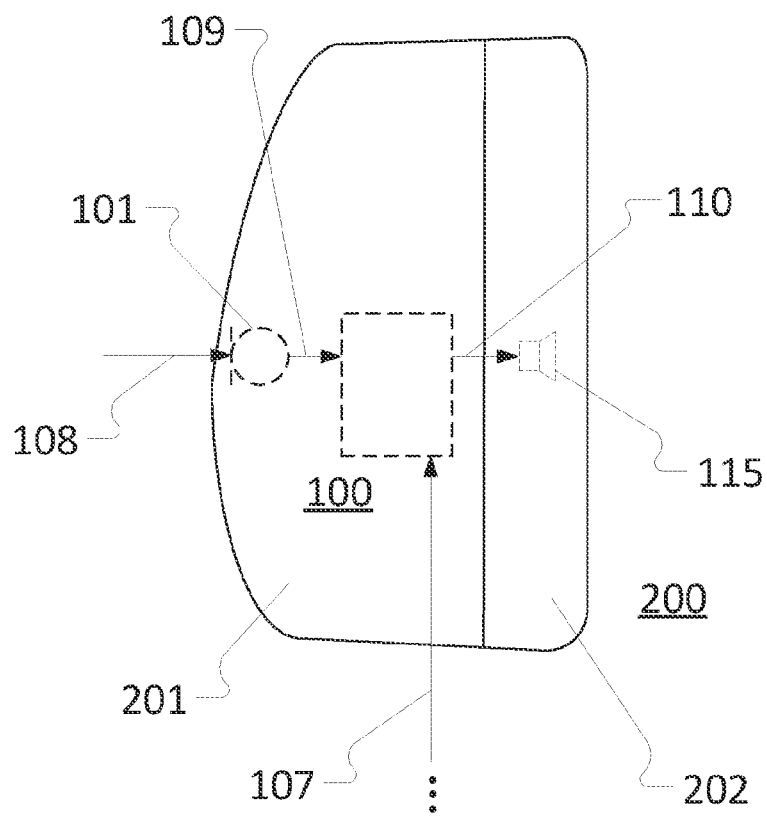

FIG. 2 schematically illustrates an audio device as disclosed herein being part of an exemplary over-the-ear cup for a hearing protection device, headset, or similar.

Illustrated in FIG. 2 is an ear cup or the like 200 that comprises an audio device 100 as disclosed herein, e.g. as shown in FIG. 1. The ear cup 200 is part of device such as a headset, a passive and/or active hearing protection device, a passive and/or active hearing protection communication headset, an ANR headset, etc. The audio device 100 may be internal (as shown) to the ear cup 200 or alternatively external. In this particular example, the ear cup 200 comprises a shell or housing 201 and a cushion, padding, or similar 202.

The shell or housing 201 comprises the audio device 100 that receives an ambient sound signal 109 from a microphone 101 picking up ambient sound 108. The microphone 101 is in this embodiment located on or in the exterior of the shell or housing 201. In at least some embodiments, the shell or housing 201 further comprises one or more sound attenuating elements that dampens at least a part of the outside ambient sound.

Furthermore, the audio device 100 receives a received radio signal 107 using a wireless or wired connection from (in this example) an external radio communications unit or element (not shown).

The audio device is connected with a speaker or the like 115 to deliver an overall sound signal 110 to the ear canal of the user as disclosed herein, e.g. in connection with FIG. 1, where the speaker or the like 115 is located in the interior of the cup 200.

Figure 3A:
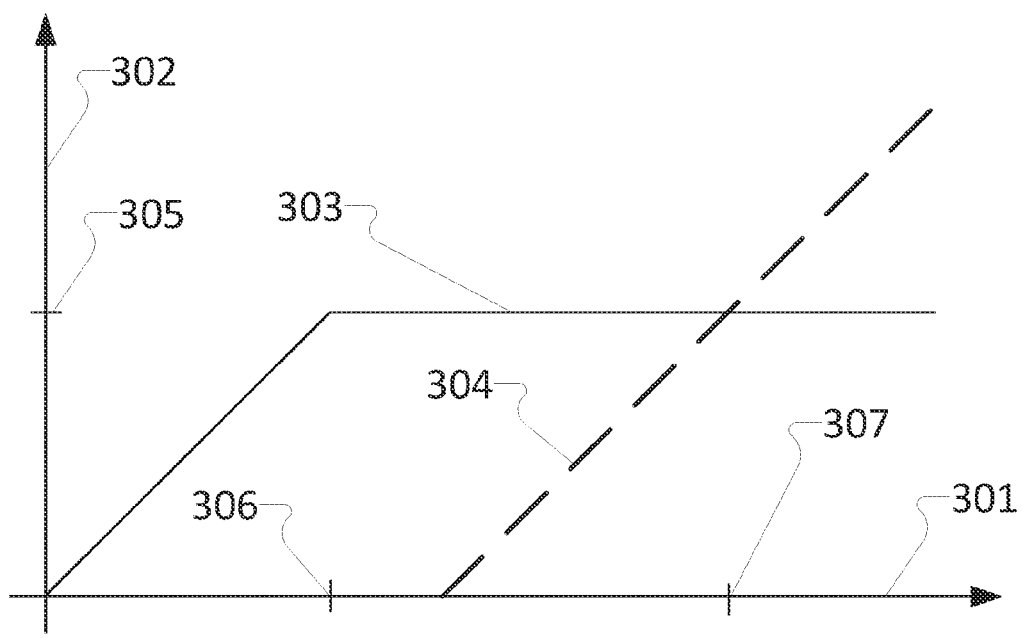
FIGS. 3a, 3b, and 3c schematically illustrate graphs illustrating different sound levels and gain values for different sound signals according to embodiments of an adaptive auto-gain element as disclosed herein.
Figure 3B:
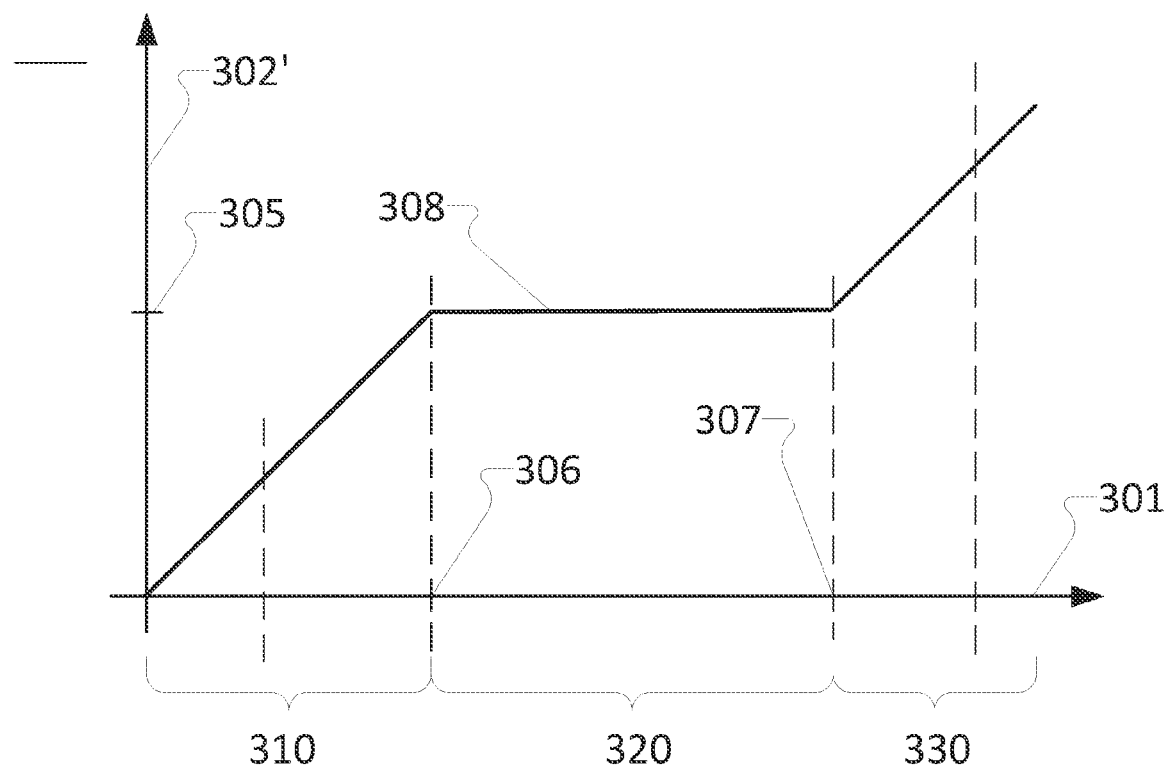

FIGS. 3a, 3b, and 3b schematically illustrate graphs illustrating different sound levels and gain values for different sound signals according to embodiments of an adaptive auto-gain element as disclosed herein.

Illustrated in FIG. 3a is a graph having a sound level of ambient sound or received ambient sound signal (corresponding to 108 or 109 in FIGS. 1, 2, and 4) as the x axis 301 and a sound level as the y axis 302 illustrating—according to some exemplary embodiments and somewhat idealised—a hear-through signal 303 (corresponding to 109' in FIGS. 1, 2, and 4) and a leakage noise signal 304 as a function of the ambient sound or received ambient sound signal (only referred to as ambient sound in the following).

As can be seen, the hear-through signal 303 increases with increasing ambient sound level until a first predetermined level 306 (e.g. about 85 dB) where it is capped to protect the hearing of a user at a maximum level 305 (typically about 85 dB). Alternatively, the hear-through signal 303 is not capped but slopped e.g. using reduction or compression according to a predetermined rate (e.g. 2:1 or other applicable rate, signifying for this particular example that the output of the hear-through signal 303 increases half as much as the input signal). The leakage noise 304 is not present for lower ambient sound levels 301 but at some point (depending on the overall sound attenuating capabilities of the specific audio device and/or the device comprising the audio device) leakage noise will be present and will increase with increasing ambient sound level. At first, sound attenuating element(s) of the audio device and/or the device comprising the audio device is normally capable of attenuating the leakage noise as well. However, at a predetermined second level 307 (depending very much on the specific design of the audio device or the device comprising the audio device), the amount of leakage noise can no longer be suppressed and a user will start to experience it (at least above a certain level). As disclosed herein and as will be explained further in connection with FIGS. 3b and 3c for an exemplary embodiment, an adaptive gain value of an auto-gain function for a received radio signal (se e.g. 107 in FIGS. 2 and 3) is adaptively controlled in response to these signals.

Illustrated in FIG. 3b is a graph corresponding to the one of FIG. 3a except that the y axis 302' now is the total sound level as experienced by the user and that an overall sound signal 308 (corresponding to 110 in FIGS. 1, 2, and 4) is illustrated. The overall sound signal 308 is the sum of the hear-through signal and the ambient sound level in FIG. 3a (see 303 and 304).

Further illustrated are three ranges 310, 320, and 330 as determined by the first and the second predetermined levels 306, 307. As disclosed herein, the gain value of the auto-gain function is adaptively set differently depending on which interval a given sound level for, in this and corresponding embodiments, the combination of the ambient sound level and the hear-through signal (i.e. the overall sound signal 308) is in. In other embodiments, the gain value is adaptively set depending on only what interval the hear-through signal is in.

In some embodiments and as disclosed herein, in a first interval 310 (when the hear-through signal is below the first predetermined level 306) the gain value for the auto-gain function is increased and decreased with respectively increasing and decreasing sound level of the overall sound signal 308. If the sound level of the overall sound signal does not change (e.g. within certain boundaries or tolerances) then the gain value does not change. Alternatively, the gain value for the auto-gain function is fixed for a part of the first interval 310 (for lower sound levels and e.g. for the lower half or other fractions) and is, for another part of the first interval 310, increased (or decreased) for increasing (or respectively decreasing) sound levels of the overall sound signal 308. This can also be seen as having a shorter first interval with a further interval (below the first) where the gain value is maintained (e.g. as illustrated in FIG. 3c).

In a second interval 320 (when the ambient sound signal is below a predetermined second level 307 and the hear-through signal is capped at a maximum level 305, i.e. when the sound level is above the predetermined first level 306), the gain value is maintained (e.g. within certain boundaries or tolerances).

In the third interval 330 (when the ambient sound signal is above the predetermined second level 307), the gain value for the auto-gain function is increased and decreased with increasing and decreasing, respectively, sound level of the overall sound signal 308. If the sound level of the overall sound signal does not change (e.g. within certain boundaries or tolerances) then the gain value does not change. Alternatively, the gain value for the auto-gain function is increased (or decreased) for increasing (or respectively decreasing) sound levels of the overall sound signal 308 for a part of the third interval 330 and is fixed for another part of the third interval 330 (for higher sound levels and e.g. for the upper half or other fractions). This can also be seen as having a shorter third interval with a(nother) further interval (above the first) where the gain value is maintained (e.g. as illustrated in FIG. 3c).

Figure 3C:
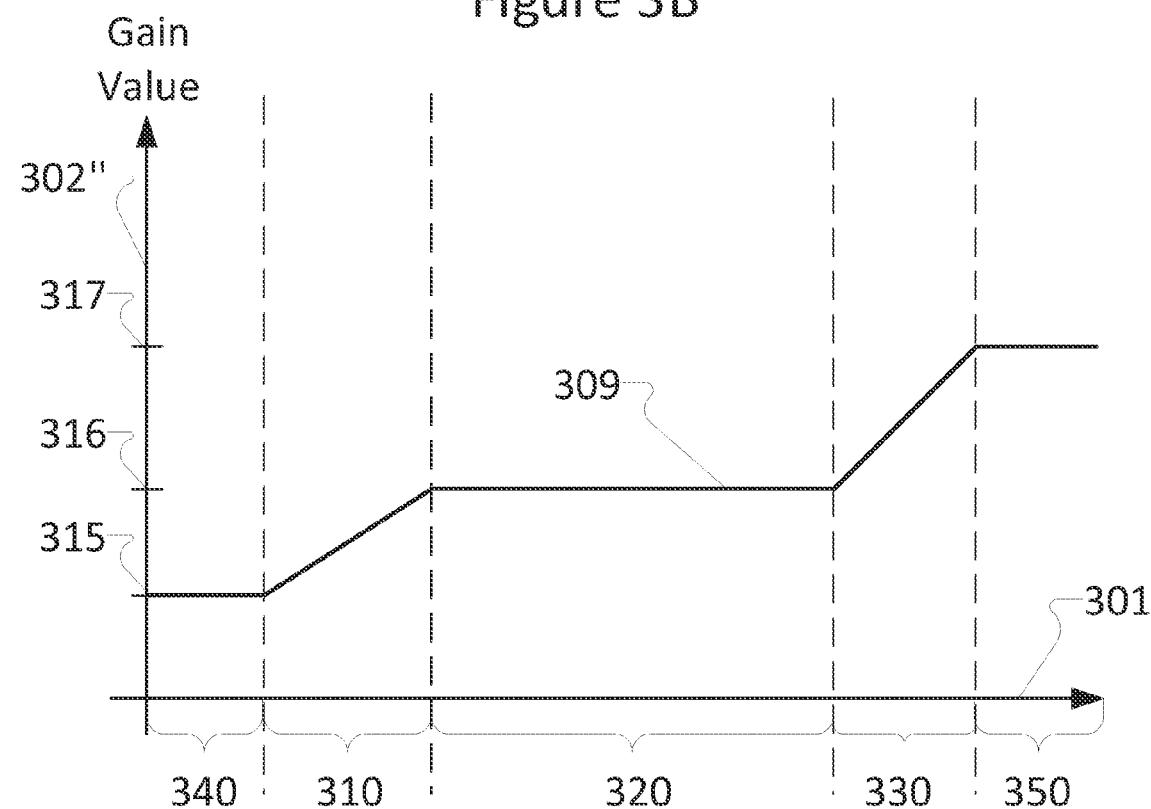

Illustrated in FIG. 3c is a graph corresponding to the ones of FIGS. 3a and 3b except that the y axis 302" now indicates the gain value (as a function of the sound level of the overall sound signal) for the auto-gain function and that a gain value signal 309 is illustrated. The x axis 301 corresponds to the one of FIGS. 3a and 3b.

Dashed lines connect FIGS. 3b and 3c to illustrate potential corresponding points for illustrative purposes. However, is should be noted that at least for some embodiments, FIGS. 3b and 3c does not necessarily relate to each other, i.e. the graph of FIG. 3b can be different for the same graph of FIG. 3c and vice versa.

FIG. 3c illustrates a first 310, second 320, and third 330 interval and two further intervals 340, 350 as described above. In a first further interval 340 for lower sound levels of the ambient sound, the gain value is—in this particular example—kept at a predetermined value 315 that e.g. may be 0 dB or about 0 dB but can be different. For this interval, the ambient noise is not very severe and there is normally no need to increase the volume of the received radio signal.

In the first interval 310, the gain value is increased (and decreased) as disclosed herein in response to the hear-through signal (and/or the received ambient sound signal) as these levels of the hear-through signal otherwise potentially could make the received radio signal less intelligible or obscured for the user.

In the second interval 320, the gain value is maintained as disclosed herein at (or about) a predetermined value 316 since the hear-through signal is kept constant (and there is no significant leakage noise present).

In the third interval 330, the gain value is increased (and decreased) as disclosed herein further as significant leakage noise now is present and the received radio signal needs to be increased further to be intelligible, etc.

In a second further interval 350 for higher sound levels of the ambient sound, the gain value maintained at a predetermined value 317 even for increasing leakage noise in order to not risk damaging the user's hearing by increasing the volume of the received radio signal further.

It is to be understood that the illustrated shapes are somewhat simplified and idealised and may be quite different depending on specific implementation and use. The shapes, slopes, etc. of the curves, the lengths and number of the intervals, etc. may e.g. be different. In particular, it is advantageously to fit a gain curve 309 to a particular use, implementation, or need. It should also be noted, that there does not need to be a 1:1 correspondence between the gain value and the level of the hear-through signal (and/or the ambient noise).

As one example, if a headset, etc. implementing an embodiment of the audio device as disclosed herein e.g. has a whisper mode functionality, the gain value in the first further interval 340 (in the example of FIG. 3c) could e.g. start to be above the predetermined value 315 for smaller sound levels of the hear-through signal and/or the ambient sound (so quieter sounds are amplified or amplified more), decrease (with increasing sound levels) until reaching the predetermined value 315 (or another value), and be maintained for the rest of the of the first further interval 340.

Furthermore, even for intervals where the gain value has been described as being maintained, the gain value can be maintained with certain relatively smaller boundaries and/or tolerances, i.e. the curve segments need not be perfectly horizontal and can have a (relatively smaller) inclination or slope.

Figure 4:
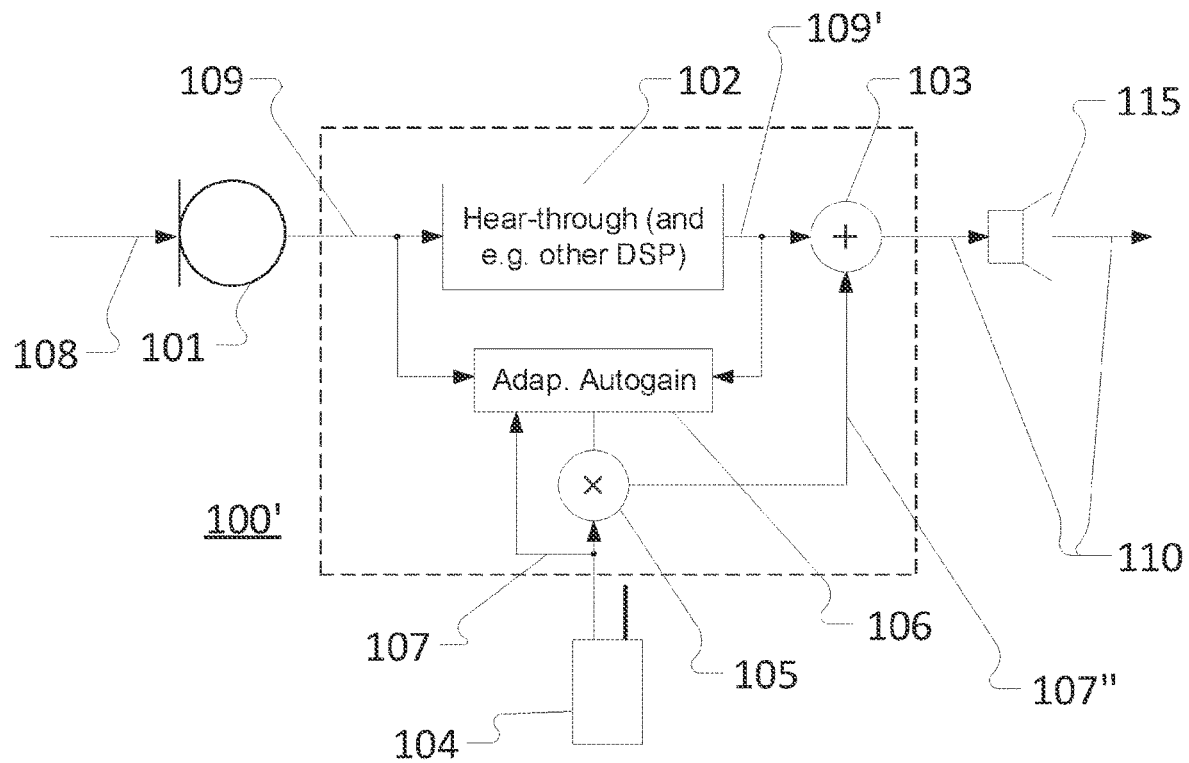
FIG. 4 schematically illustrates an audio device comprising an adaptive auto-gain element as disclosed herein according to another embodiment.

FIG. 4 schematically illustrates an audio device comprising an adaptive auto-gain element as disclosed herein according to another embodiment.

Illustrated is an audio device 100 corresponding to the one of FIG. 1 and as disclosed herein where the adaptive auto-gain element 106 is configured to set the adaptive gain value for the auto-gain function in response to the received radio signal (i.e. in addition to at least the hear-through signal) and for some embodiments in response to a target level of the received radio signal resulting in a further modified radio signal 107" being different than the modified radio signal 107' of FIG. 1.

In the shown embodiment, the adaptive auto-gain element 106 is configured to receive the received radio signal 107. Alternatively, the adaptive auto-gain element 106 may be connected to the (internal or external) radio communications element 104.

As another alternative, the adaptive auto-gain element 106 may be configured to receive a sound level and/or a target level of the received radio signal.

In some further embodiments, the gain value is not set in response to the hear-through signal, i.e. only in response to the received radio signal (and e.g. further signals).

In the claims, any reference signs placed between parentheses shall not be constructed as limiting the claim. The word "comprising" does not exclude the presence of elements or steps other than those listed in a claim. The word "a" or "an" preceding an element does not exclude the presence of a plurality of such elements.

The mere fact that certain measures are recited in mutually different dependent claims does not indicate that a combination of these measures cannot be used to an advantage.

It will be apparent to a person skilled in the art that the various embodiments of the invention as disclosed and/or elements thereof can be combined without departing from the scope of the invention as defined in the claims.

The invention claimed is:

1. An audio device for receiving radio communication, the audio device
    being configured to receive radio communication as a received radio signal, the radio communication including audio,
    wherein the audio device comprises
        a hear-through element configured to provide a hear-through signal to a user in response to a received ambient sound signal, and
        an adaptive auto-gain element configured
            to perform an auto-gain function of the received radio signal according to an adaptive gain value resulting in a modified radio signal,
            to set the adaptive gain value for the auto-gain function in response to the hear-through signal,
            to maintain the adaptive gain value for the auto-gain function at a current level when the hear-through signal would otherwise be above but kept about a predetermined first level and the received ambient sound signal is below a predetermined second level, wherein the predetermined second level is higher than the predetermined first level, and
            to adaptively increase and decrease, respectively, the adaptive gain value for the auto-gain function as a function of
                the hear-through signal, and/or the received ambient sound signal, when the received ambient sound signal is above the predetermined second level or a predetermined third level;

an adding element configured to add the audio of the modified radio signal with the hear-through signal to produce an overall sound signal that is provided to a speaker.

2. The audio device according to claim 1, wherein the audio device further comprises one or more sound attenuating elements configured to dampen at least a part of ambient sound outside the audio device.

3. The audio device according to claim 2, wherein the one or more sound attenuating elements comprises one or more passive hearing protection elements configured to dampen the received ambient sound signal and/or the hear-through signal, and/or one or more active hearing protection elements configured to selectively dampen the received ambient sound signal and/or the hear-through signal, the selectively dampening of the received ambient sound signal and/or the hear-through signal being carried out according to one or more predetermined criteria, and/or an active noise reduction system configured to reduce or suppress noise in the received ambient sound signal and/or the hear-through signal.

4. The audio device according to claim 1, wherein the adaptive auto-gain element is further configured to set the adaptive gain value for the auto-gain function in response to an estimated amount of leakage noise present in an ear-canal of the user.

5. The audio device according to claim 4, wherein the audio device is configured to measure or estimate a sound level of the received ambient sound signal and/or the hear-through signal, and derive the estimated amount of leakage noise in response to the measured or estimated sound level(s).

6. The audio device according to claim 1, wherein the adaptive auto-gain element is further configured to set the adaptive gain value for the auto-gain function in response to the received ambient sound signal.

7. The audio device according to claim 1, wherein the adaptive auto-gain element is configured to adaptively increase and decrease, respectively, the adaptive gain value for the auto-gain function as a function of the hear-through signal when the hear-through signal is below a predetermined first level.

8. The audio device according to claim 7, wherein the adaptive auto-gain element is configured to maintain the adaptive gain value for the auto-gain function at a current level when the hear-through signal would otherwise be above but kept about the predetermined first level or another predetermined level and the received ambient sound signal is below a predetermined second level.

9. The audio device according to claim 8, wherein the predetermined second level is larger than the predetermined first level.

10. The audio device according to claim 8, wherein the predetermined first level is about 85 dB and/or the predetermined second level is selected from the range of about 95 dB to about 115 dB, is selected from the range of about 100 dB to about 110 dB, or is about 105 dB.

11. The audio device according to claim 1, wherein the audio device is configured to maintain the adaptive gain value of the auto-gain function at a level providing optimised signal to noise ratio between the received radio signal and an overall sound signal present in an ear canal of the user, the overall sound signal comprising at least the modified radio signal and the hear-through signal.

12. The audio device according to claim 11, wherein the audio device comprises or is connected to a microphone located in the ear canal of the user, and wherein the signal to noise ratio is determined by measuring a level of the received radio signal or the modified radio signal and by measuring a level of the overall sound signal in the ear canal of the user.

13. The audio device according to claim 11, wherein the signal to noise ratio is determined in response to an estimate of the noise in the ear canal of the user.

14. The audio device according to claim 1, wherein the audio device comprises a radio communications element being configured to receive radio communication and supply the received radio signal, or is configured to receive the received radio signal from an external radio communications element.

15. The audio device according to claim 1, wherein the audio device is an active and/or passive hearing protection communication headset, and/or an active noise reduction headset.

16. The audio device according to claim 1, wherein the adaptive gain value as a function of the hear-through signal is set or fitted in dependence to one or more functional capabilities and/or intended use.

17. The audio device according to claim 1, wherein the hear-through element and/or another processing element of the audio device is configured to perform one or more digital signal processing functions selected from the group consisting of:

occlusion, providing increased situational awareness, compensating for hearing loss, providing additional radio signals from additional radio sources, whisper-mode, comfort mode, environment detection and adaption, noise reduction, noise gate, spatial filtering or beamforming, volume control, tinnitus maskers, voice prompts, or other injected audio signals, noise cancellation, and linear filtering.

18. The audio device according to claim 1, wherein the adaptive auto-gain element is configured to set the adaptive gain value for the auto-gain function in response to the received radio signal.

19. The audio device according to claim 18, wherein the adaptive gain value for the auto-gain function is set in response to a target level of the received radio signal.

20. The audio device according to claim 1, wherein the predetermined first level is about 85 dB and/or the predetermined second level is selected from the range of about 95 dB to about 115 dB, is selected from the range of about 100 dB to about 110 dB, or is about 105 dB.

* * * * *